(12) United States Patent
Joseph

(10) Patent No.: US 11,071,562 B2
(45) Date of Patent: Jul. 27, 2021

(54) REUSABLE UNIVERSAL TISSUE MORCELLATOR SYSTEM

(71) Applicant: Lalu Joseph, Ernakulam-Kochi (IN)

(72) Inventor: Lalu Joseph, Ernakulam-Kochi (IN)

( * ) Notice: Subject to any disclaimer, the term of this patent is extended or adjusted under 35 U.S.C. 154(b) by 140 days.

(21) Appl. No.: 16/062,100

(22) PCT Filed: Jan. 30, 2017

(86) PCT No.: PCT/IN2017/000023
§ 371 (c)(1),
(2) Date: Jul. 12, 2018

(87) PCT Pub. No.: WO2017/145176
PCT Pub. Date: Aug. 31, 2017

(65) Prior Publication Data
US 2018/0368871 A1 Dec. 27, 2018

(30) Foreign Application Priority Data

Feb. 25, 2016 (IN) .............................. 201641006496

(51) Int. Cl.
*A61B 17/32* (2006.01)
*A61B 17/34* (2006.01)
(Continued)

(52) U.S. Cl.
CPC .... *A61B 17/32002* (2013.01); *A61B 17/3439* (2013.01); *A61B 17/3496* (2013.01); *A61B 2017/0046* (2013.01); *A61B 2017/00119* (2013.01); *A61B 2017/00199* (2013.01); *A61B 2017/00212* (2013.01); *A61B 2017/00398* (2013.01); *A61B 2017/00464* (2013.01);
(Continued)

(58) Field of Classification Search
CPC .. A61B 17/32002; A61B 2017/320024; A61B 17/3439; A61B 17/3494; A61B 17/3496
See application file for complete search history.

(56) References Cited

U.S. PATENT DOCUMENTS

| | | | |
|---|---|---|---|
| 10,028,762 B1 * | 7/2018 | Slupchynskyj | .. A61B 17/32002 |
| 2006/0047185 A1 * | 3/2006 | Shener | ............... A61B 1/00068 |
| | | | 600/156 |

(Continued)

*Primary Examiner* — Wade Miles
(74) *Attorney, Agent, or Firm* — The Law Firm of AQ Basit

(57) ABSTRACT

The present invention relates to an improved reusable universal tissue morcellator system. It comprises of a hollow tubed morcellator hand piece locked with flexible rotor cable connected to Motor Drive Unit, having a control panel with a touch screen and manual operating system in the same unit, with inbuilt installation tutorial videos and procedure videos having audio alarms with speed control and activation features using foot pedal or remote control. MDU is addition-ally provided with an external USB port for software and program updating. The cylindrical head of the rotor cable is inserted and locked into the tubular hollow area of the morcellator handle. Morcellator hand piece is having same diameter trocar head (203*b*), which can be assembled with cannula tube of varying diameter and length, so as to use interchangeable cutter blades of different diameter and length. The trocar head is provided with gas inflow/irrigation inlets.

20 Claims, 11 Drawing Sheets

Figure 1:
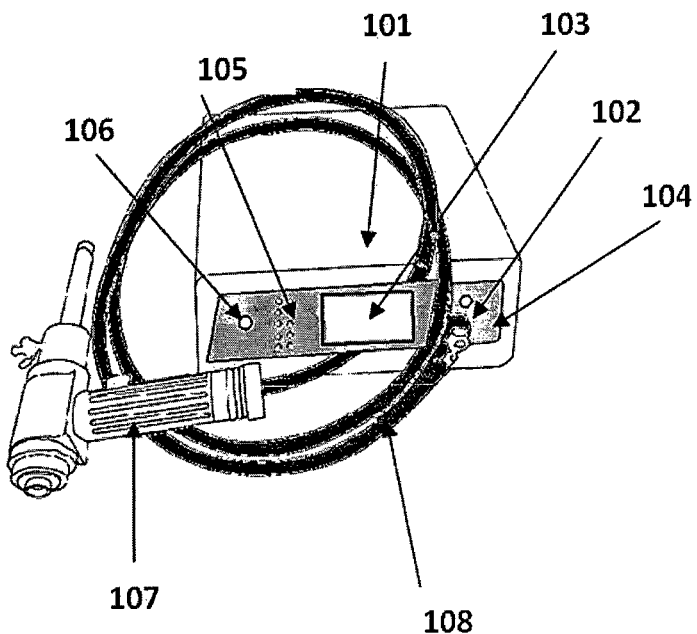

(51) Int. Cl.
*A61B 17/00* (2006.01)
*A61B 90/00* (2016.01)
(52) U.S. Cl.
CPC ............ *A61B 2017/00477* (2013.01); *A61B 2017/00973* (2013.01); *A61B 2017/320024* (2013.01); *A61B 2090/0801* (2016.02); *A61B 2090/08021* (2016.02); *A61B 2217/007* (2013.01)

(56) References Cited

U.S. PATENT DOCUMENTS

2012/0016399 A1* 1/2012 Poulsen ......... A61B 17/320758
606/170
2012/0209273 A1* 8/2012 Zaretzka ........ A61B 17/320725
606/80

* cited by examiner

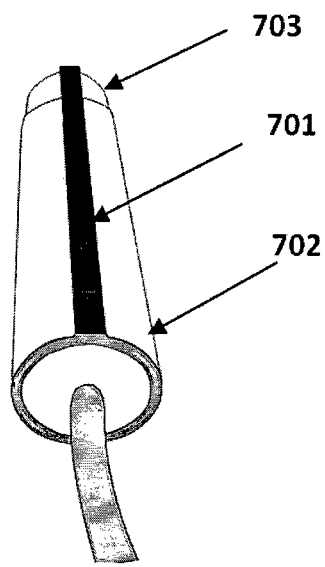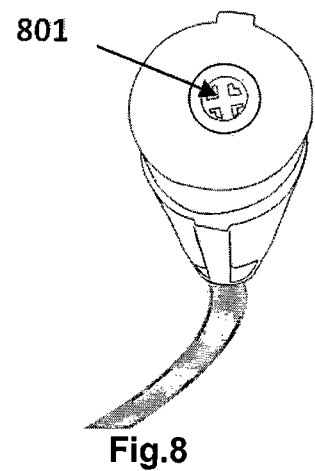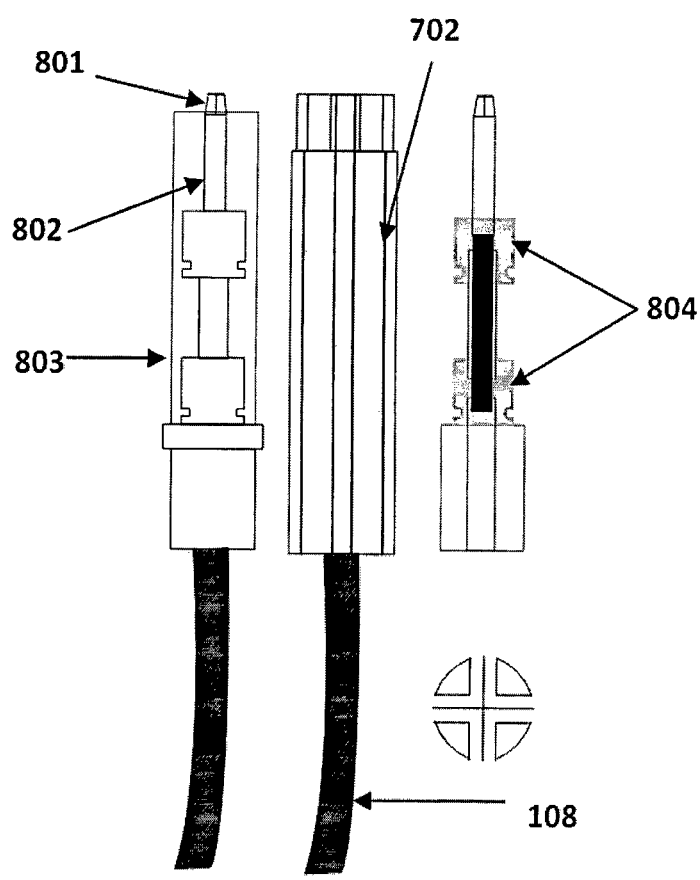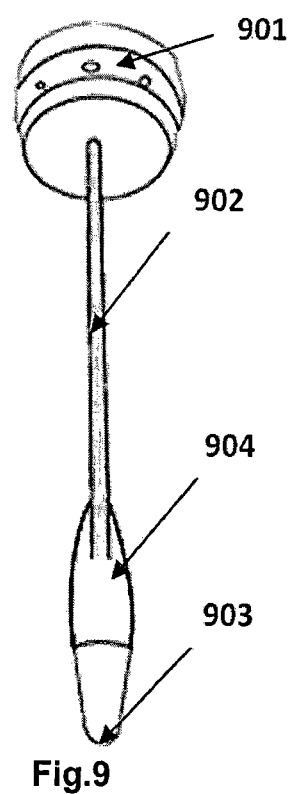
Fig.7
Fig.8
Fig.8(a)
Fig.9

REUSABLE UNIVERSAL TISSUE MORCELLATOR SYSTEM

FIELD OF INVENTION

The present invention generally relates to morcellator used in laparoscopic surgery with improved reusable tissue morcellator, more especially an universal tissue morecellator provided with morcellator hand piece having same diameter trocar head, which can be assembled with cannula tube of varying diameter and length, so as to use interchangeable cutter blades. Trocar head is provided with gas inflow/irrigation inlets. In addition the motor drive unit is having both manual and touch screen operating system. Further it is having procedure video tutorials and audio alarms with speed control and provision for activation using foot pedal or remote control. It can be operated manually using the switches provided on the control panel and or by operating the morcellator handle button provided therein. MDU is having an external USB port for software and program updating.

BACKGROUND OF THE INVENTION

Laparoscopic morcellation is commonly used at surgery to remove bulky specimens from the abdomen using minimally invasive techniques. Historically, morcellation was performed using a device that required the surgeon or assistant to manually 'squeeze' the handle. Other reports describe using a scalpel directly through the abdomen to create small specimens that can be drawn out of the abdominal cavity. In 1993, the first electric morcellator was introduced in the US market. It was initially used for uterine extraction, but later applied to other organs. The use of morcellator at surgery has now become common. Despite decades of experience, there remains limited understanding of the short-term and long-term disadvantages of morcellation. Concerns have been raised about injury to surrounding organs including bowel, bladder, ureters, pancreas, spleen and major vascular structures. Long-term issues may include parasitic growth of retained tissue with the potential to cause adhesions, cause bowel dysfunction and potentially disseminate unrecognized cancer.

Morcellation is associated with spreading of cellular material of the morcellated tissue. In gynecologic surgery for benign pathologies there is approximately a 0.09~0.1% risk of an unexpected leiomyosarcoma. After morcellation 64% of such cases may develop disseminated disease which is of particular concern because of the considerable mortality of leiomyosarcoma. Morcellation of the more frequent benign leiomyoma variants that may also cause disseminated disease, which while not associated with increased mortality is frequently inoperable and therefore much more difficult to manage than the original disease.

Such disadvantages due to spillage during morcellation can be reduced significantly by using the Safety Isolation Bags for in-bag morcellation. The other disadvantages of the present morcellators are as follows:

There is no built in gas-inflow/irrigation inlet which allows the creation of pneumoperitoneum using the morcellator while doing in-bag tissue retrieval.

There is no scope for interchangeability of the morcellator hand piece using the same morcellator handle. For example, a 18 mm or 22 mm morcellator hand piece will work only with corresponding handle having 18 mm or 22 mm size.

There is no audio information on RPM and alerts during procedure in the prior art morcellator.

There is no option to make use of the same handle for hand pieces of different diameters and length for the removal of different sizes of tissues during surgery.

There is no in built video tutorial showing procedure of morcellation, as well as in-bag morcellation and user guide provided in any of the prior art motor drive unit.

There is no in built video tutorial showing procedure of morcellation, as well as in-bag morcellation and user guide provided in any of the prior art motor drive unit.

There is no provision with both manual and touch screen operating systems in the same motor drive unit and speed control by foot pedal, or by using buttons on the morcellator handle and remote controller for speed and volume.

To obviate the above draw back, I have come out with the improved reusable tissue morcellator system which has morcellator trocar sheaths with provision for gas inflow/irrigation inlets, in addition to having the provision for making it to varying size of the morcellator hand piece of different diameter and length viz 4 mm, 6 mm 10 mm, 15 mm, 18 mm and 22 mm with the same handle by connecting at the front end of the handle provided with thread. Further the new motor drive unit is provided with 4 inch to 10 inch wide touch screen with inbuilt installation tutorial videos and procedure videos having audio alerts and with a default setting of 600 RPM which can be increased up to 3000 RPM. However, if the surgeon wants to reduce the speed, it can be reduced to 50 RPM. The new motor drive unit is provided with both manual and touch screen operating facilities in the same unit. Procedure video tutorials, audio alarms and provision for speed control are also provided in the motor unit. Activation by using foot pedal or remote control or manually operating the switches on the control panel and or the morcellator handle are also provided. External USB port also is provided in the motor unit, USB port is provided for editing or updating the software and programs of the touch screen interface.

SUMMARY

The present invention relates to an improved reusable universal tissue morcellator system. It comprises of a hollow tubed morcellator hand piece (107) locked with flexible rotor cable (108) connected to Motor Drive Unit (MDU) (101) of the morcellator on one side and morcellator hand piece consisting of morcellator trocar sheath (203) having trocar head (203b) and trocar cannula tube (203a) on the other side through which cutter blade (FIG. 6, 6a) or obturator (FIG. 9) is inserted and connected to the MDU using the rotor cable. The speciality of the instant invention rests with the following special features.

Figures 6, 6A:
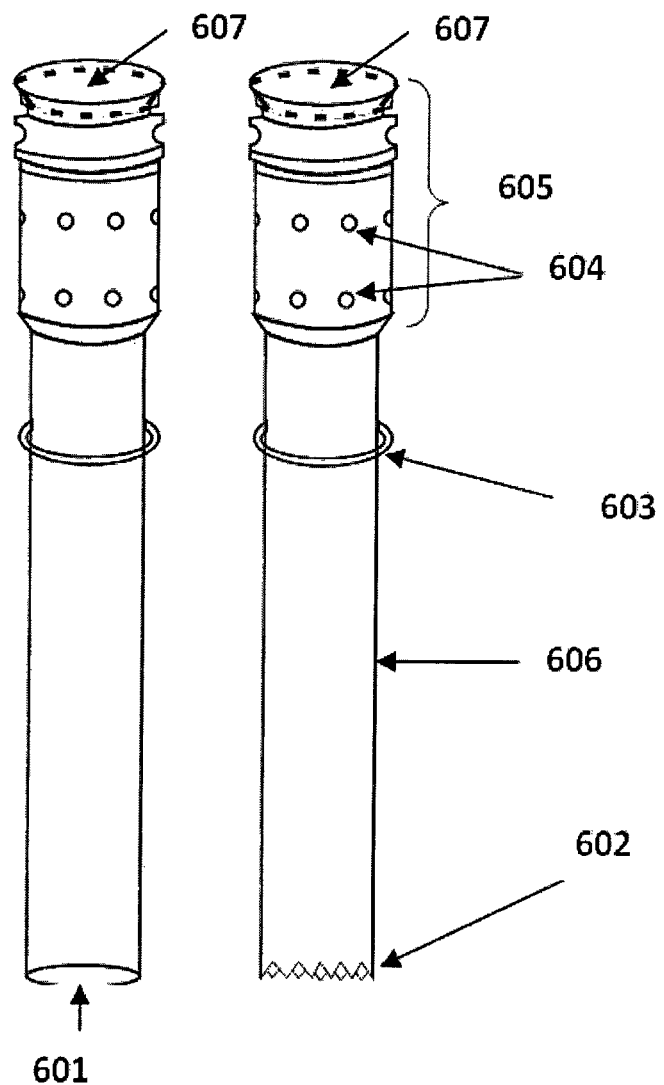
Figure 6B:
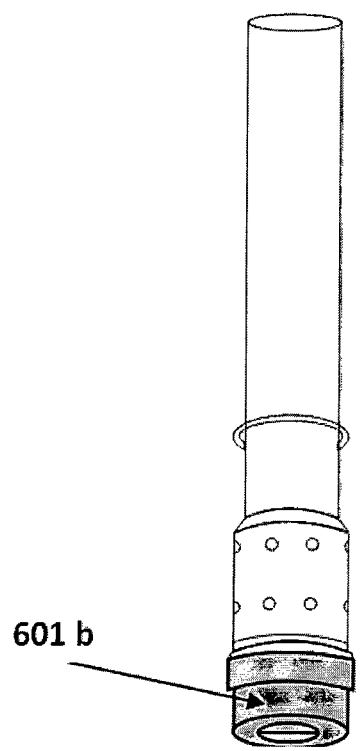
Figure 6C:
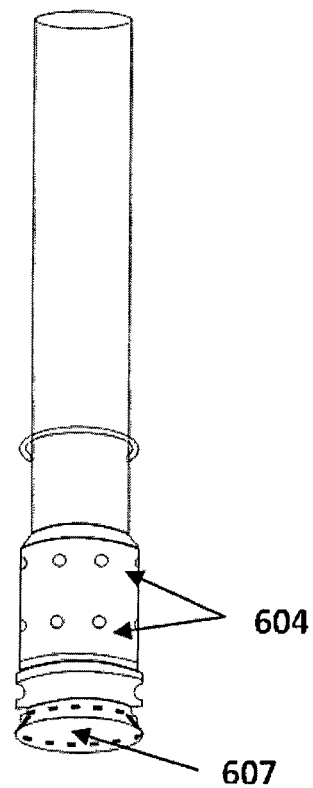

Morcellator hand piece is of varying size and having a fixed size handle with interchangeable trocar sheath, provided with internal threading for assembling to the morcellator handle (FIG. 4), having same diameter trocar head (203b), but with different diameter of size 4 mm, 6 mm, 10 mm, 15 mm, 18 mm and 22 mm and length of size 4 to 18 cm cannula tube (203a), so that interchangeable cutter blades can be fixed to the same morcellator handle thereby facilitating the use of different size cutter blades based on the requirement during specific procedures forming morcellator hand pieces of 4 to 18 cm effective length with varying diameters of size 4 mm, 6 mm, 10 mm, 15 mm, 18 mm and 22 mm (FIG. 6).

Cutter blade is having cutter blade head (605) with a two sets of pin-holes (604), with the first set of holes to enable the blade to keep in deactivated position while not in use during morcellation and the second set of holes to keep the cutter blade locked to the handle so that the cutting edge is exposed and ready to cut while morcellation and also with double step projections with grooves (601 *c*) to place the double decker washer having double locking projections (113).

Obturator is having a head end (901) on one end with one set of pinholes so that it will get locked to the morcellator handle once inserted properly, conical blunt tip (903) with reverse tapering (904) on the other end with and a rod (902) connected in between the two ends;

The double decker pneumoseal washer placed on the morcellator cutter blade head end is having two separate diaphragms and the upper diaphragm is having 4 mm to 20 mm diameter, chosen based on the hand instruments used, single straight cut opening (111*a*) in the center within a circular projection (111*b*) and the bottom diaphragm (112) which is one to two cm below the upper diaphragm with a cross cut multi flap opening (112*a*) at the middle with 4 mm to 20 mm diameters to enable the passage of the tenaculam/hand-instruments and also to block gas leakage once the instrument is withdrawn through the washer.

Motor drive unit is having a control panel (104) with a touch screen operating system (103) as well as manual operating system (105) having 4 to 10 inch wide touch screen with inbuilt installation tutorial videos and procedure videos having audio alerts and with a default setting of 600 RPM which is increasable up to 3000 RPM in addition to having the provision to reduce the speed up to 50 RPM as well as with provision for selecting speed control and activation manually or remotely and an USB port (108*a*) also is provided for editing or updating the programs of the touch screen interface.

In a preferred embodiment under the invention the exposed portion of the head end of the cutter blade is covered, once the cutter blade is inserted and locked with "morcellator handle head cap" (121) provided with a 25 mm diameter opening at the head-end (123) for inserting hand instruments to extract tissues while morcellation and a threaded mouth (124) to fix it to the morcellator handle.

BRIEF DESCRIPTION OF THE DRAWINGS/FIGURES

These objectives and other features, aspects, and advantages of the present invention will be better understood when the detailed description is read with reference to the following drawings according to a preferred embodiment under the invention.

FIG. 1: Isometric view of the full assembly of the improved reusable tissue morcellator system according to the invention, wherein 101—Motor Drive Unit (MDU) of the morcellator; 102—Rotor cable connection port of the MDU; 103—Touch screen interphase on the control panel; 104—Control panel of MDU; 105—manual operating switches on the control panel; 106—ON/OFF button on the front panel for touch screen; 107—Morcellator handle assembled with trocar sheath and cutter blade connected to the MDU using the rotor cable; 108—Flexible rotor cable connected to the MDU and morcellator handle.

FIG. 1 (*a*): Another isometric view of the fully assembled improved reusable tissue morcellator system with touch screen and manual operating system viewed from the back side with speed control and enabling the activation by foot pedal. Wherein 101*a*—the foot pedal connecting port on the MDU; 102*a*—power cord connecting port on the back side of the MDU; 103*a*—ON/OF power switch on the MDU; 104*a*—speed control buttons on the foot pedal; 105*a*—motor activation switch on the foot pedal; 106*a*—system cooler fan on the MDU; 107*a*—audio alarm speaker; 108*a*—USB port for editing or updating the software and programs of the touch screen interface.

FIG. 1 (*b*): Shows the remote control unit for speed and volume control

Figure 2:
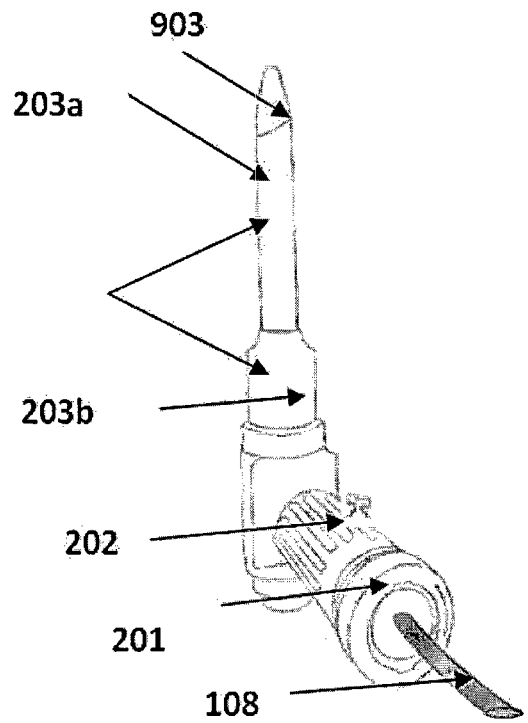

FIG. 2: Isometric view of the morcellator handle connected with obturator, trocar sheath and rotor cable, wherein 201—Handle lock for rotor cable's cylindrical head; 202—Morcellator handle's holding area; 203—The trocar sheath having a uniform head with same diameter provided with internal threads matching with that of the morcellator handle and welded to cannula tubes having different diameters; 203*a*—Trocar cannula tube; 203*b*—trocar head; 903 blunt tip of the obturator which is passed through the morcellator hand piece.

FIG. 2(*a*): Another isometric view of the morcellator handle being assembled with obturator, trocar and rotor cable, wherein 702—. Cylindrical head of the rotor cable for inserting into the hollow tube 201(*b*) of the handle and 202*a*—the speed control button on the morcellator handle.

FIG. 2 (*b*)—Yet another view of the morcellator handle with obturator and trocar sheath assembled, wherein 201*b*—Hollow tube of the Morcellator handle where the rotor cable's cylindrical head will be inserted and locked.

FIG. 2(*c*): Shows the morcellator trocar sheath with gas inflow inlet connected to the morcellator handle, wherein 502*a*—Oblique cut of the trocar sheath which will act as the core guard; 501*a*—Gas inflow/irrigation inlet of the morcellator trocar sheath.

Figure 3:
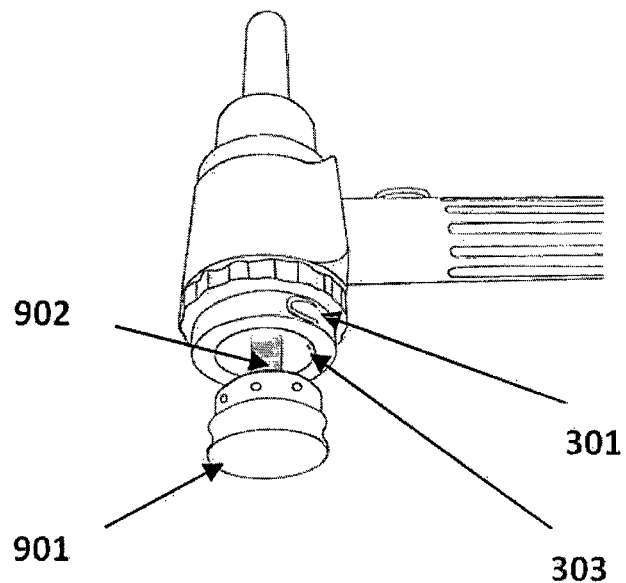

FIG. 3: Shows the blunt tip obturator getting inserted through the insertion slot of the Morcellator handle at the back side into the hand piece that is connected to the trocar sheath, wherein 301—The cutter Blade/Obturator unlock button at the back end of the morcellator handle; 902—Obturator rod; 901—Obturator head with locking pin holes; 303—Obturator/cutter blade insertion area of the handle.

FIG. 3(*a*): Shows the inner view of the back end of the morcellator handle, wherein 301—The unlocking button made of stainless steel at the cutter blade/obturator insertion area; 302—The locking pin at the obturator/cutter blade insertion area; 303—The cutter blade/obturator insertion area of the handle and 304—Rotor locking knob inside the morcellator handle's hollow-tube end, which gets locked to the adapter lock mechanism 801 of the cylindrical head of the rotor cable FIG. 8.

Figures 4, 5:
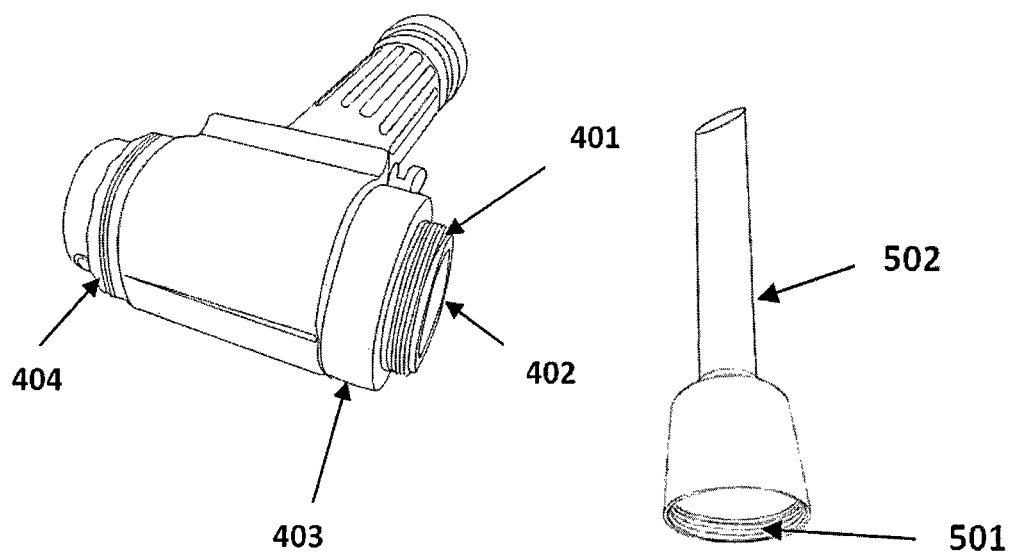

FIG. 4: Shows morcellator handle with threaded ring assembly for connecting to the front end of the morcellator handle, wherein 401—Threads of the threaded ring portion; 402—Front end opening of the threaded ring having outer diameter 24 mm to 28 mm; 403—Body of the threaded ring assembly; 404—provision for fixing the "morcellator handle head cap".

FIG. 5: Shows the morcellator trocar sheath without gas inflow/irrigation inlet, wherein 501—Internally threaded portion of the trocar sheath head; 502—Trocar sheath cannula tube.

Figure 5A:
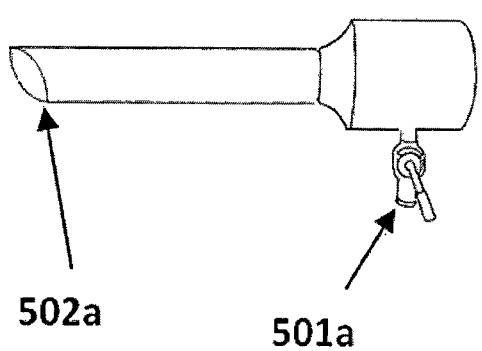
Figure 5B:
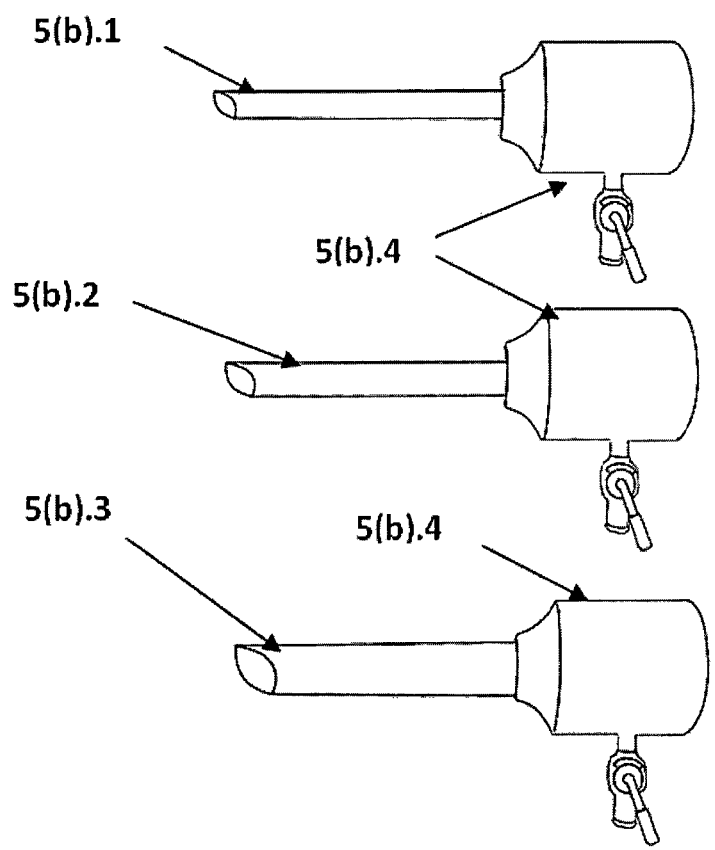

FIG. 5(*a*): Shows the morcellator trocar sheath with gas inflow/irrigation inlet, wherein 501*a*—gas inflow/irrigation inlet of the morcellator trocar sheath; 502*a*—Oblique cut of the trocar sheath which will act as the core guard once the cutter blade is inserted through the hand piece and covered by the trocar sheath FIG. 5(b): Shows the trocar sheaths having uniformly internally threaded head with same diameter and cannula tubes with different diameters wherein 5(b).1, 5(b).2, and 5(b).3 shows different diameter trocar sheath with same dia trocar head 5(b).4.

FIGS. 6 and 6(a) Shows morcellator cutter tube blades with sharp round edge and serrated cutting edge respectively, wherein 601—Round sharp edge of the cutting tube; 602—Serrated sharp edge of the cutting tube; 603—Stopper ring welded on the outer side of the cutter tube; 604—two set of locking pin holes (6 to 10 Nos each) on the morcellator cutter tube head; 605—Head end of the morcellator cutter tubes; 606 Cutter tube; 607 circular entry hole of the cutter blade head.

FIG. 6 (b): Shows morcellator cutter blade head with two step pin-hole locking arrangement with double decker pneumoseal washer wherein 601b—double decker pneumoseal washer.

Figure 6D:
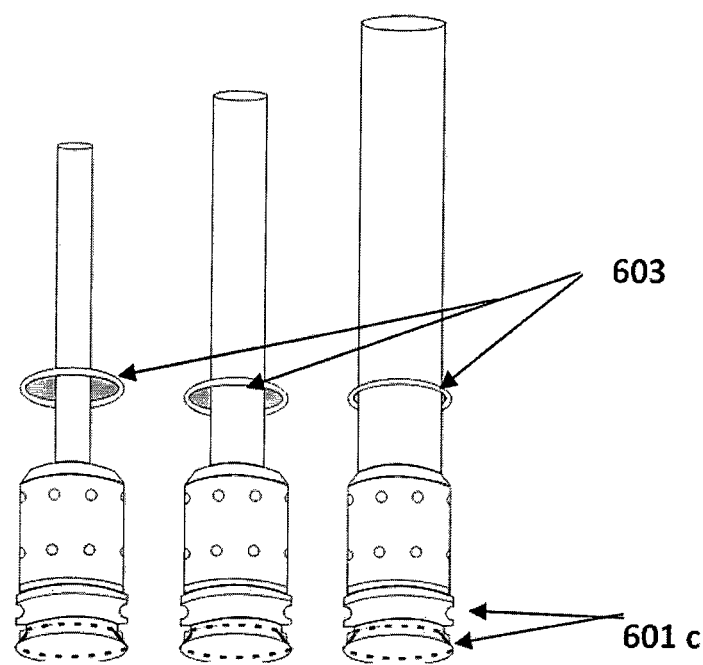
Figure 6E:
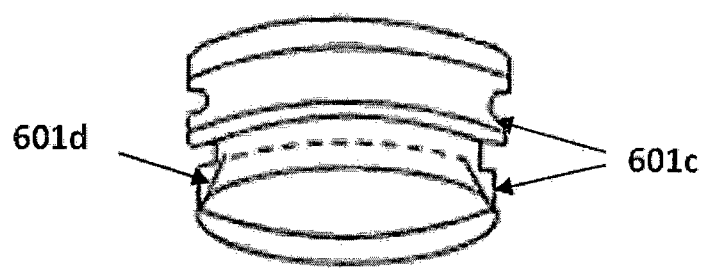

FIG. 6 (c): Shows morcellator cutter blade head with two step pin-hole locking arrangement wherein 604—Two set of locking pin holes (6 to 10 Nos each) on the morcellator cutter tube head. 607—circular entry hole of the cutter blade head FIG. 6(d): Shows the cutter blade head with a two sets of pin-holes, with the first set of holes to enable the blade to keep in deactivated position while not in use during morcellation and the second set of holes to keep the cutter blade locked to the handle so that the cutting edge is exposed and ready to cut while morcellation; 601c—Head portion of the cutter blade with double groove projections to fix the double decker washer; and 603—the stopper rings welded on to the cutter tubes.

FIG. 6 (e): Shows the enlarged view of the double groove projection of the cutter blade head wherein 601d—Chamfered portion at the entry hole 607 which is 10 to 25 degree for the easy opening and closing of the valves in the inner diaphragm of the double decker washer once inserted and while in morcellation.

FIG. 7: Shows the cylindrical head of the Morcellator rotor cable connected to the flexible cable, wherein 701—The vertical projection on the body of the cylindrical head of the rotor cable enabling proper locking, once placed inside the tubular hollow area 201b of the morcellator handle; 702—Body of the cylindrical head of the rotor cable; 703—Head end of the rotor cable's cylindrical portion.

Figure 2A:
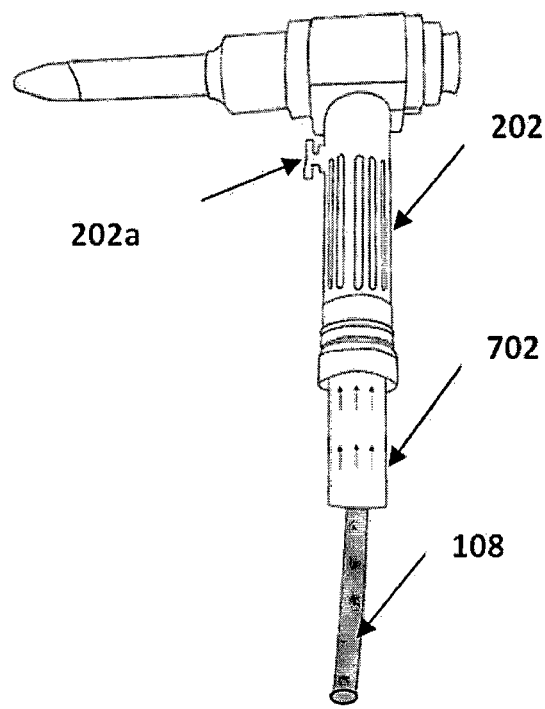

FIG. 8: Shows isometric view of the adaptor lock mechanism of the rotor cable's cylindrical head, wherein 801—The adaptor lock mechanism of rotor cable's cylindrical head which get locked and connected to the rotor locking knob 304 of the morcellator handle;

FIG. 8(a): internal view of the cylindrical head of the rotor cable; showing how the adapter lock mechanism is assembled and connected to the flexible rotor cable wherein 801—adaptor lock mechanism; 802—metallic tube of 4-8 mm diameter and 2 to 5 cm length having cross cut groove to a depth of about 1 cm at one end; 803—acrylic tube, inside this tube the assembly is packed and covered and packed tightly within a cylindrical body (702) so that it will go and closely get placed into the hollow tube 201(b) of the morcellator handle as shown in FIG. 2 or 2(a) and wherein the adaptor lock mechanism will get locked to the rotor locking knob inside the morcellator handle; 804—ball-bearing assembly; 108 flexible rotor cable.

FIG. 9: Shows the blunt tip conical obturator with locking pin-holes, wherein 901—of the obturator with locking pin-holes; 902—Rod of the obturator which is fitted to the head of the obturator at one end and welded to the conical blunt tip on other end; 903—Conical Blunt tip of the obturator; 904—Reverse tapered portion of the conical blunt tip towards rod end to facilitate dilating the incision made on the abdominal cavity.

Figures 10, 10A:
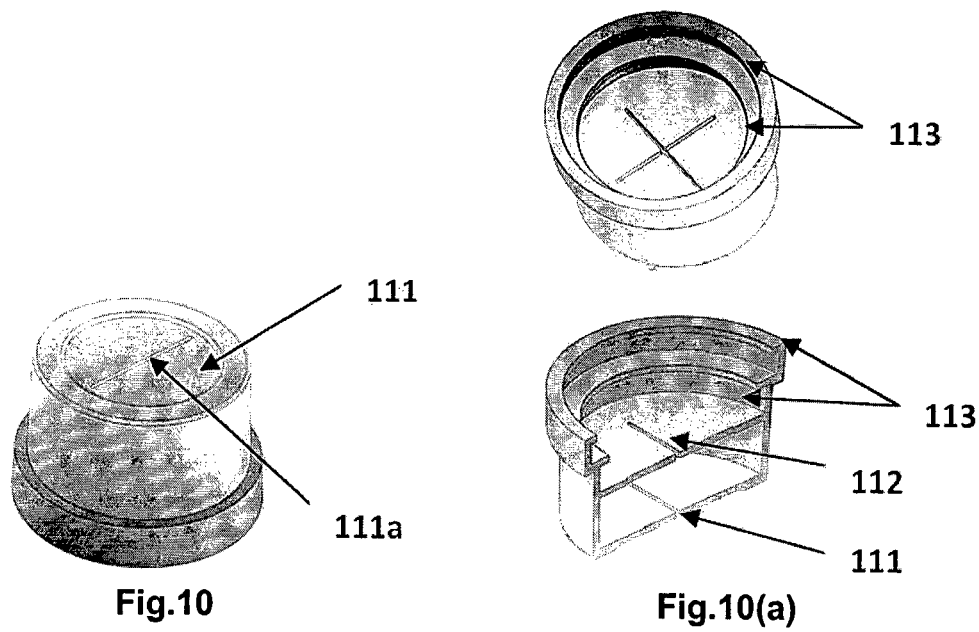

FIG. 10: Shows the isometric external view of the double decker pneumoseal washer, wherein 111—the outer diaphragm and 111(a) outer opening with a straight cut on the upper layer within a rounded projection.

FIG. 10(a): Shows the isometric external view of the double decker pneumoseal washer as well as cross sectional view of the double decker pneumoseal washer having two separate pneumoseal diaphragms, wherein 111—upper layer within a rounded projection having outer opening with a straight cut to prevent tearing off of the washer. 112—Inner multi flap pnuemoseal valve made with a cross cut of the double decker pneumoseal washer which cans also act as pneumoseal and 113—Bottom portion with two steps locking projections of the double decker pneumoseal washer.

Figures 10B, 10C:
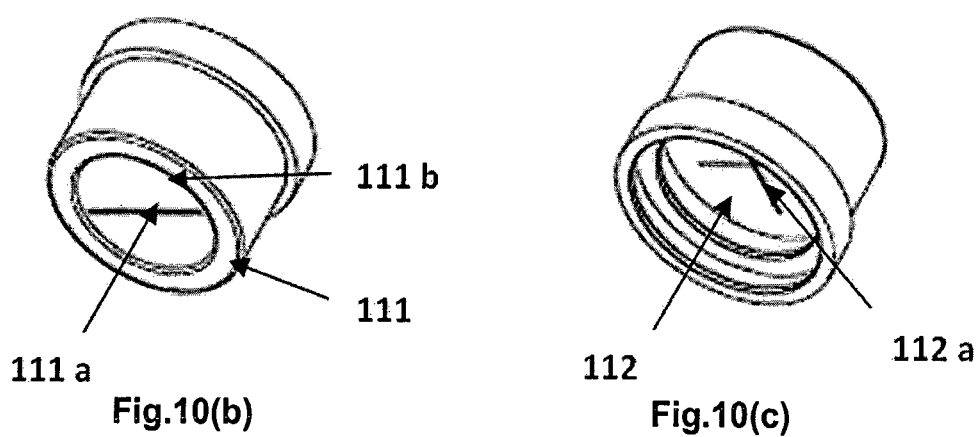

FIG. 10(b): Shows the external view of double decker washer with outer straight—cut opening wherein 111a—outer opening with a straight cut; 111b—rounded projection; 111—upper layer.

Figure 11:
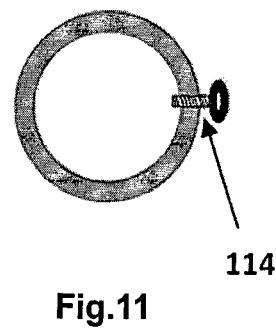

FIG. 10(c): Shows the internal view of the double decker washer with inner multi flap layer opening wherein 112—Inner multi flap pnuemoseal valve; 112a—cross cut of the double decker pneumoseal washer;

FIG. 11: Shows the "length adjusting ring of the morcellator hand piece", wherein 114—Tightening/loosening screw.

Figure 11A:
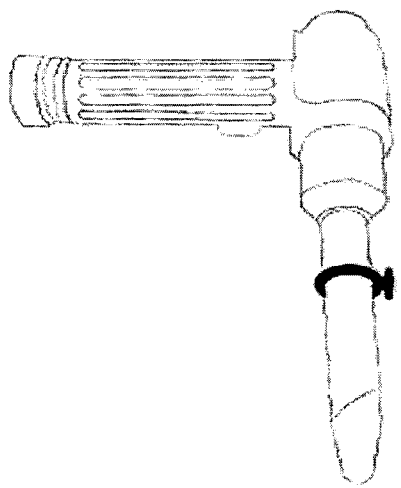

FIG. 11(a): Shows the "length adjusting ring of the morcellator hand piece" placed on the assembled morcellator trocar cannula tube.

Figure 12:
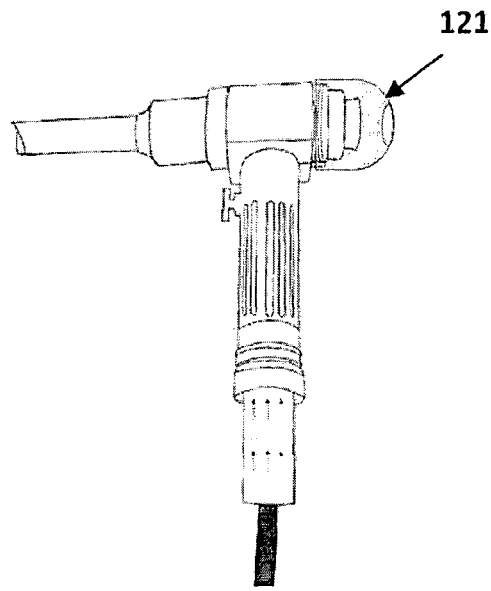

FIG. 12 Shows the assembled morcellator hand piece unit covered with "morcellator handle head cap" at the cutter blade/obturator insertion area of the handle wherein, 121—morcellator handle head cap which is screwed to the threaded ring 122 connected at the head end of the handle to protect the rotating cutter blade from accidental contact of the surgeon's hand or other instruments while morcellation.

Figure 12A:
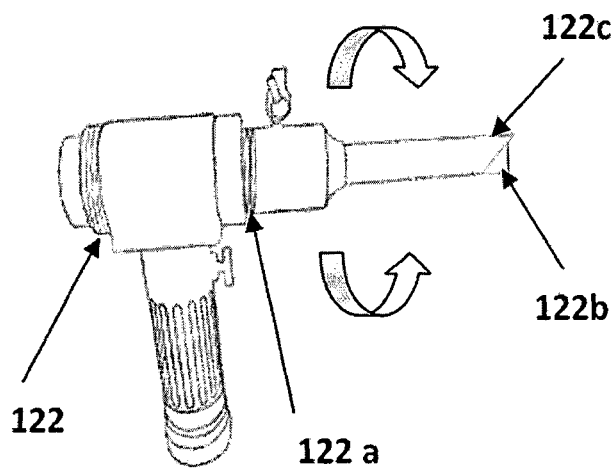

FIG. 12(a) Shows the hand piece assembly with a threaded ring 122 at the head end of the handle to fix the "morcellator handle head cap", wherein 122 (a) shows the trocar sheath which is rotatable to suitable position and 122b shows the cutter blade tip inside the core guard.

Figure 12B:
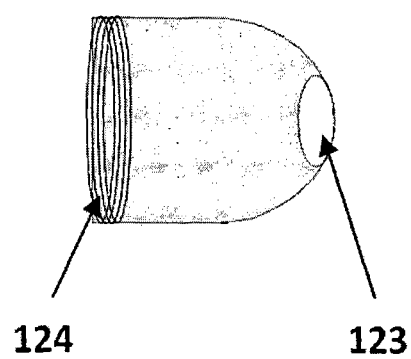

FIG. 12(b) Shows the external view of the "morcellator handle head cap", wherein 123—25 mm diameter opening at the head-end for inserting hand instruments to extract tissues while morcellation and a threaded mouth 124; to fix to the morcellator handle.

DETAILED DESCRIPTION OF THE INVENTION

Features of the present invention will become apparent to those skilled in the art upon reading the following detailed description of the instant invention.

The improved reusable universal tissue morcellator system according to the present invention has interchangeable cutter blades, outer trocar sheath with gas-inflow and irrigation features. The motor drive unit provided therein is provided with 4" to 10" wide touch screen with inbuilt installation tutorial videos and procedure videos having audio alerts. There is provision to set the speed of rotation of the cutter blade with a default setting of 600 RPM which can be increased up to 3000 RPM. However if the surgeon wants, the speed can be reduced to 50 RPM. And the motor drive unit is provided with both manual and touch screen operating facilities with speed control and activation facility manually using foot pedal or remote controller. Speed control can also be done either using the switch provided in the hand piece handle or using the touch screen.

As shown in FIG. 1, the full assembly of tissue morcellator system the Motor Drive Unit, MDU (101) is having a control panel (104) with a touch screen operating system (103) and a manual operating system (105) on the same control panel to which one end of the flexible rotor cable (108) is connected. The other end of the rotor cable provided with the cylindrical head is inserted and locked in to the tubular hollow area of the morcellator handle (201b) provided with adaptor lock mechanism (801) of the rotor cables cylindrical head (702) connected to the rotor locking knob (304) inside the hollow tube of the morcellator handle. The handle is locked with the rotor cable's cylindrical head once inserted inside the handle followed by locking with handle locking ring (201). The front end of the handle having an externally threaded portion (401) is connected to the Morcellator Trocar sheath (FIG. 5 (a)) with. Gas inflow/irrigation inlet (501a). This forms the morcellator hand piece and the cutter blade is inserted through the cutter blade/obturator insertion area (303) provided with a locking pin (302)/an unlocking button (301) mechanism made of stainless steel at the back side of the handle.

The motor drive unit is with touch screen operating systems and an interactive interface. Once the power switch of the front panel is made ON, it displays screen of 4 to 10 inches display with windows for product usage, tutorial and procedure video applications. The motor drive unit is with a default speed set as 600 RPM and can be increased up to 3000 RPM depending on the need of the surgery. If the surgeon wants a much lesser speed, it can be reduced up to 50 RPM. The new improved motor drive unit also provides an interactive audio support so that the surgeon could every time hear the RPM settings or any warning alarms/indicators like over heating or overload as the morcellator motor drive unit will be kept at the back side of the surgeon during surgery to avoid the twisting of the rotor cable which normally happens, if it is placed in front of the surgeon while morcellation. Additionally an external USB port (108a) is provided for editing or updating the software and programs of the touch screen interface.

According to another embodiment under the invention, the motor drive unit is also having a manual operating system apart from the touch screen display, with RPM indicators and manual operating buttons (105) as shown in the FIG. 1. The Motor Drive unit is designed in such a way that it is usable in urological surgeries (TURP), in addition to gynecological surgeries and general surgeries, by altering the programs on the control panel.

Figure 1A:
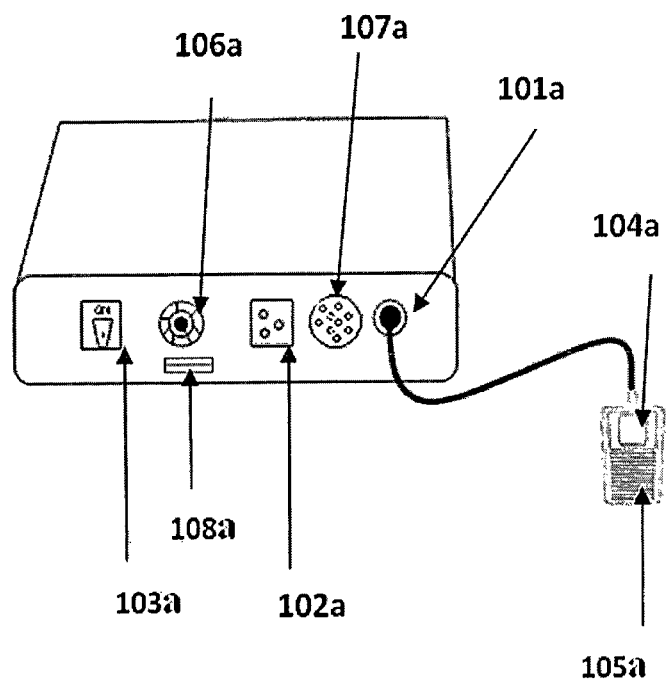
Figure 1B:
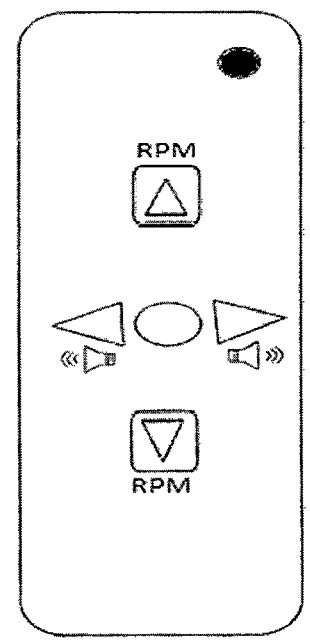

According to another embodiment under the invention, as shown in FIG. 1(a) the motor drive unit provides an audio alarm on cutting speed and other interactive features and warning alarms/indicators like over heating or overload (107a). The activation of the motor and speed control during morcellation can be done using the buttons on the control panel or by using the button on the handle (202a) or on the foot pedal 104(a) and 105(a) and or with a remote controller as shown in FIG. 1(b).

The morcellator handle is assembled with the cylindrical head (702) of the flexible rotor cable (108) which is inserted into the hollow tube 201(b) of the handle and locked. As shown in FIG. 2 the morcellator handle is provided with holding area (202) and handle lock (201) to lock the rotor cable with the handle. The obturator with the conical blunt tip (903) is locked inside the morcellator handle with the pin locking mechanism. The obturator is inserted through the backside of the morcellator handle after connecting trocar sheath on the threaded portion at the front side of the morcellator handle. There are different sizes and type of trocar sheaths as shown in FIG. 5 (b), with same head diameter provided with uniform internal thread and with different tube diameter with or without gas in-flow inlet and with different length so that it can be fixed to the same morcellator handle. This facilitates the use of different size trocar sheath based on the requirement during specific procedures.

As shown in FIG. 2 (a) the cylindrical head 702 of the rotor cable is getting inserted into the hollow tube 201b of the morcellator handle and the adaptor lock mechanism of the rotor cable (801) gets locked to the rotor knob (304).

Figure 2B:
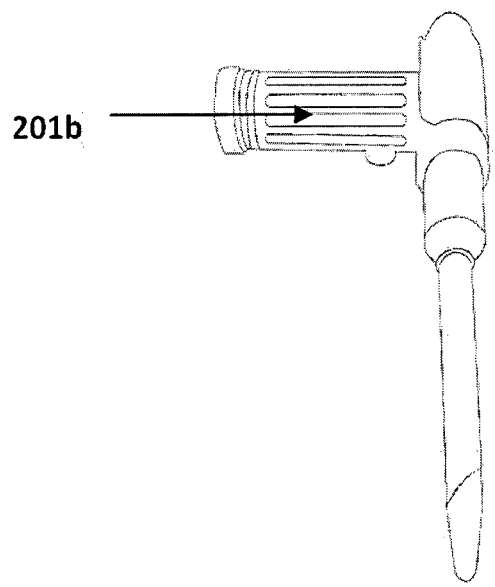

FIG. 2(b) shows the hollow tubular area 201(b) of the Morcellator handle where the Rotor cable's cylindrical head (702) will be inserted.

Figure 2C:
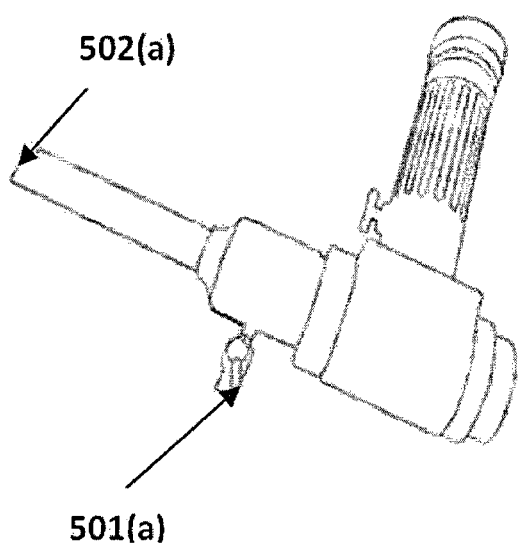

Referring to FIG. 2(c) the morcellator trocar sheath is having same diameter internally threaded trocar head but is having different diameter cannula tube with gas inflow/irrigation inlet (501a) that is connected to the threaded portion (401) at the front end of the morcellator handle which will work as the outer sheath for the cutter blade and also as the core guard to prevent coring of tissues. There is a provision to change the core-guard position by rotating the trocar sheath over the threaded portion (401) as per the need of morcellation. Sometimes during surgery surgeons need to change the core-guard position to anterior/posterior/right side/left side of the fibroid to facilitate proper morcellation without coring the tissues and for proper vision of the tip of the cutter blade throughout the surgery.

FIG. 3: Shows the blunt tip obturator getting inserted into the hand piece through the insertion slot of the morcellator handle at the back side, wherein the cutter blade/Obturator unlock button (301) is provided at the back end of the morcellator handle. Obturator head (901) is having 6-10 numbers of locking pin holes.

Figure 3A:
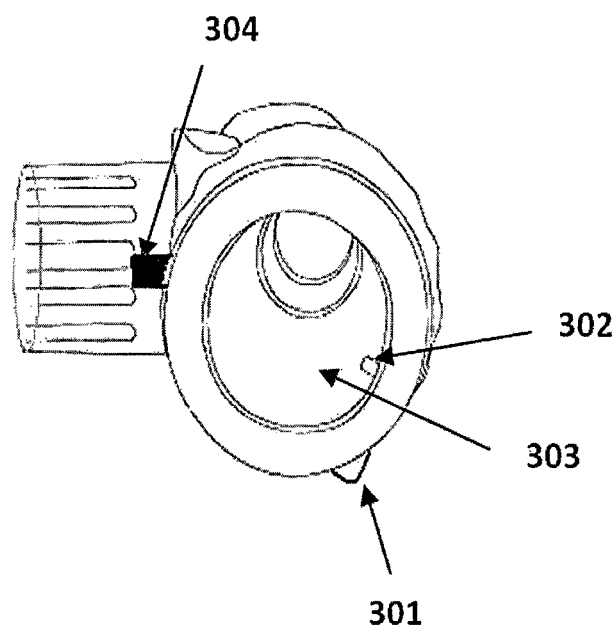

The inner view of the back end of the morcellator handle, with the cutter blade/obturator insertion area (303) with locking pin (302)/unlocking button (301) is shown in FIG. 3(a). They are made of stainless steel. The adaptor lock mechanism (801) of the rotor cable's cylindrical head get locked automatically by means of the "rotor locking knob" (304) of the morcellator handle Inside the hollow tube once inserted.

As shown in FIG. 4, the front end of the morcellator handle is connected with a threaded ring assembly. The threaded ring has a higher diameter portion with an internal thread which is matching with the external threaded portion of the front end (402) of the morcellator handle and the low diameter portion having external threaded portion is matching with internal threaded portion of the trocar head (501). The morcellator trocar sheath is provided with gas inflow/irrigation inlet and connected to the threaded ring portion in the front end of the morcellator handle. Back end of the morcellator handle is having a provision to fix the "morcellator handle head cap" 404.

As shown in FIG. 5 the morcellator trocar sheath with cannula tube (502) is having internally threaded head portion (501) without gas-inflow/irrigation which matching to the external threaded front end of the morcellator handle so that different sizes of trocars sheaths can be connected to the same morcellator handle.

FIG. 5 (a) shows the morcellator trocar sheath having same diameter internally threaded head with gas inflow/ irrigation inlet (501*a*). The distal end of the trocar cannula tube is (502*a*) obliquely cut which will act as the core guard to enable pealing of tissues during morcellation to avoid accidental coring of tissues and for proper vision of the tip of the cutter blade throughout the procedure.

As shown in FIG. 5 (*b*) the morcellator trocar sheaths are with different diameter cannula tubes 5(*b*).1; 5(*b*) 2; 5(*b*).3, but with same diameter for the trocar head 5(*b*).4 and the trocar cannula tube are of different lengths to enable the effective morcellator hand piece length of 4 cm to 18 cm as per the need of the surgery.

As shown in FIG. 6, 6(*a*), 6(*b*), 6(*c*) and 6(*d*) the morcellator cutter blade tubes are of different lengths and diameters to enable the effective morcellator-hand piece length varying from 4 to 18 cm and cutter blades matching for hand pieces with diameters of 4 mm, 6 mm, 10 mm, 15 mm, 18 mm and 22 mm. The Cutter blade head and stopper rings are of same diameter in each size cutter blade with similar pin-holes 604 and chamfering of 10 to 25 degree at the head opening 601(*d*) but with different diameter cutter tubes to make them 4 mm/6 mm/10 mm/15 mm/18 mm and 22 mm diameter with sharp round cutting edge (601)/or sharp serrated cutting edge (602) at the front end and is having higher diameter head end (605) with two set of 6-10 locking pin holes (604) and double step projections with groove (601*c*) to place the double decker washers to prevent gas leakage during morcellation. Stopper ring (603) is welded on to the outer side of the cutter tube to stabilize the cutter tube while rotating during morcellation and the stopper ring is provided at 4 to 8 cm from the nearest set of pin holes of the cutter blade head. On the head of the cutter tube there are two sets of 6-10 pin holes given, which is 1 to 3 cm apart. The first set of holes enables the blade to keep in deactivated position while not in use when inserted and locked into the handle and the second set of holes is to keep the cutter blade locked to the handle so that the cutter end is exposed for cutting while morcellation.

On the cutter tube head, the circular inner hole entry (607) into the cutter blade is chamfered, 10 to 25 degree (601*d*) to enable the free opening and closing of the inner valve diaphragms of the double decker washer while inserting and withdrawing the hand instrument through the cutter blade during morcellation. Specially matching double step projections with grooves 601(*c*) are given on the head of the cutter blade to enable double locking (113) of the double decker washer for enhanced fitting so that the washer will not come out easily during extraction of tissues as shown in FIG. 6(*e*).

FIGS. 6(*b*) and 6 (*c*) show the morcellator cutter blade head with two set of locking pin-holes (604) and double decker pneumoseal washer (601*b*) placed on the head end. The double decker pneumoseal washer is having two separate diaphragms 111 and 112. The upper diaphragm is having 4 mm to 20 mm single straight cut opening in the center 111(*a*) within a circular projection 111(*b*) for the entry of the hand-instrument/tenaculam for extracting the tissues as well as for preventing any leak. The bottom diaphragm which is one to two cm below the upper diaphragm with a cross cut at the middle 112(*a*) with 4 mm to 20 mm diameters to enable the passage of the tenaculam/hand-instruments and also to block gas leakage once the instrument is withdrawn through the washer as it is connected at the head end projections of the cutter blade.

FIG. 6(*d*) shows the cutter blades with different diameters and lengths with two set of pin holes with the first set of holes to enable the blade to keep in deactivated position while not in use when inserted and locked into the handle and the second set of holes to keep the cutter blade locked to the handle so that the cutter end is exposed for cutting while morcellation. Also showing double step projections with grooves 601(*c*) to place and fix double decker washer and the stopper rings 603 on the cutter tubes.

The cylindrical head of the rotor cable (703) is connected to the flexible rotor cable is shown in FIG. 7 wherein vertical projection (701) on the cylindrical head of the rotor cable is provided to stabilize and immobilize it, once the body of the cylindrical head of the rotor cable (702) is inserted inside the hollow area of the morcellator handle 201(*b*) and locked with the locking ring on the handle (201). The "adapter lock mechanism" (801) of the rotor cable gets locked to the "rotor locking knob" (304) automatically, once it is inserted.

FIG. 8 shows "The adaptor lock mechanism" of the rotor cable's cylindrical head (801) which get locked and connected to the "rotor locking knob" (304) of the morcellator handle; wherein 801 is the adaptor lock mechanism of the rotor cable assembly which will get locked to the rotor locking knob inside the morcellator handle, once it is inserted and placed properly. The proper locking of the "adapter lock mechanism" to the "rotor locking knob" enables the rotation of the rotor cable and thereby the cutter blade, once the motor drive unit is switched ON and activated for carrying out morcellation.

FIG. 8 (*a*). According to a preferred embodiment under the invention, the cylindrical head of the rotor cable is made by welding the adaptor lock mechanism (801). The adaptor lock mechanism comprising of a metallic tube of 4-8 mm diameter and 2 to 5 cm length having cross cut groove to a depth of about 1 cm (802) at one end and the other end is welded to the metallic portion of the inner flexible rotor cable and assembled inside an acrylic tube (803) within 2 to 3 ball-bearing assembly (804) and covered and packed tightly within a cylindrical body (702) so that it will go and closely get placed into the hollow tube 201(*b*) of the morcellator handle as shown in FIG. 2 or 2(*a*) and wherein the adaptor lock mechanism (801) will get locked to the rotor locking knob (304) inside the morcellator handle.

As shown in FIG. 9, the head end (901) of the blunt tip conical obturator is having 6-10 Nos. of pinholes so that it will get locked to the morcellator handle once inserted properly. Rode of the obturator (902) is connected to the head end having pin holes on one end and the other end of the rode is welded to the conical blunt tip (903) with reverse tapering (904). There are obturators of different diameters and lengths to match the hand pieces.

The external views of the double decker pneumoseal washer as well as sectional view of the inner multi flap diaphragm of the double decker washer are shown in FIG. 10 and FIG. 10(*a*). The inner opening (112*a*) of the valve is made with 4 flaps and the external opening is made with single cut (111*a*) and it is not in line with the inside cutting, enabling better pneumoseal effect.

As shown in FIG. 10(*b*) the external view of the straight cut opening on the outer diaphragm (111*a*) of the double decker washer is to be connected to the back end of the cutter blade. It is having two separate diaphragms in which the upper diaphragm 111 is with an opening with a straight cut 111(*a*) within a circular projection (111*b*) to prevent the tearing-off of the washer and with a diameter of 4 mm-20 mm, decided based on the hand instruments used to pass through the cutter blade while morcellation. It enables the passage of the tenaculam/hand instruments and it blocks gas leakage once the instrument is withdrawn through the washer. The instruments are inserted through the outer opening (111*a*) of the double decker pneumoseal washer. Inner diaphragm with a cross cut multi flap opening (112*a*)

of the double decker pneumoseal washer as shown FIG. 10(c) act as an additional pneumoseal when the instruments are withdrawn. The bottom portion of the washer is with double locking projections (113) as shown in FIG. 10(a) which gets tightly fixed on the cutter tubes' double step projections with grooves (601c) on its head.

FIG. 10 (c) shows the internal view of the inner multi flap diaphragm (112) with a cross cut (112a). A double step projection, (113) is made on the inner side of the double decker washer specifically matching to enable—double locking of the washer for enhanced fitting of the washer on the cutter tube so that the washer will not come out easily during extraction of tissues.

As shown in FIGS. 11 and 11(a) the "length adjusting ring" of the morcellator hand piece is placed on the assembled morcellator trocar cannula tube, by which the surgeon can adjust portion of the hand piece needed to be inside the abdominal cavity during the morcellation procedure. The length adjusting ring is made up of fibre, Teflon or stainless steel with threaded screw. Once inserted over the trocar tube, the ring can be tightened as per the length needed by the surgeon during morcellation.

FIG. 12 shows the "morcellator handle head cap" fixed on the morcellator handle head, after the cutter blade is inserted into the hand piece through the backside cutter blade insertion area (303). The exposed portion of the head end of the cutter blade can be covered with "morcellator handle head cap" (121). By covering the cutter blade head, it will protect the surgeons hand or any instruments from accidentally touching to the rotating cutter blade head during morcellation.

FIG. 12 (a) shows the hand piece assembly with a threaded ring (122) at the head end of the handle to fix the "morcellator handle head cap". The trocar sheath is adjustable to change the core guard position while morcellation by turning it over the threaded portion on which the trocar sheath is connected (122a)

FIG. 12 (b) shows the "morcellator handle head cap" with a 25 mm diameter opening at the head-end (123) for inserting hand instruments to extract tissues while morcellation and a threaded mouth (124) to fix it to the morcellator handle.

In a preferred embodiment under the invention, the way the morcellator is assembled and made ready for morcellation and how is used during the procedure are given in the following paragraphs.

The rotor cable with its cylindrical head (702) is inserted into the hollow tubular area of the morcellator handle 201b and once inserted fully; the locking ring (201) on the handle is turned to lock the assembly as shown in FIGS. 2 and 2(a). The adapter lock mechanism (801) of the cylindrical head of the rotor cable will get engaged with the rotor locking knob (304) of the morcellator handle and that will enable the rotation of the cutter blade which is inserted into the handle and get locked with the locking pin (302). Though the trocar sheath is having different dia cannula tube (203a) selectable from [FIG. 5/5(a)/5(b)] 4 mm, 6 mm, 10 mm, 15 mm, 18 mm and 22 mm, the trocar head (203b) is having same diameter and uniform internal threading (501) with or without gas inflow/irrigation inlet and having different length to enable the effective morcellator hand piece length of 4-18 cm.

The trocar sheath will perform as the outer cover for the cutter blades (122c) with nail like projection at the tip which will work as core guard (502a). The trocar sheath is connected to the threaded ring which is attached at the front side of the Morcellator handle as shown in FIG. 4. Now this forms the assembled morcellator hand piece without cutter blades as shown in FIG. 2(c).

The obturator device having blunted conical tip and with pinhole locking arrangement and rounded head (FIG. 9) is inserted into the Morcellator hand piece through the obturator/cutter blade insertion area (303) which is at the back end of the handle. The obturator is fully inserted (FIG. 2a/2b) so that the pin-hole locking mechanism get locked to the locking pin of the handle (302) and the blunt conical tip will enable the hand piece to push it into the abdominal cavity through the morcellation port without causing trauma to the tissues and also without applying pressure at the handle end.

Once the hand piece along with the obturator is introduced and entered into the abdominal cavity, the obturator from the hand piece can be withdrawn by pressing the unlock button, as shown in (FIG. 3).

Now select the cutter blade of corresponding diameter and length (FIGS. 6 6a, 6b, 6c and 6d) which is matching to the trocar already connected to the handle to make it a hand piece set of either 4 mm/6 mm/10 mm/15 mm/18 mm or 22 mm. Introduce the selected cutter blade through the cutter blade/obturator insertion area (303) and lock it with the pin lock mechanism of the handle (302). Then using the "length adjusting ring" (FIG. 11) on the morcellator hand piece, the length of the handpiece or the portion of the hand piece needed to be inside the abdominal cavity can be adjusted. Said "length adjusting ring" placed on the trocar cannula tube of the morcellator hand piece, once tightened with an adjustable screw, the surgeon can adjust the length of the portion of the hand piece to be inside the patient's body during different stages of the procedure as shown in (FIG. 11a). The "morcellator handle head cap" is fixed at the back end of the morcellator handle as (FIG. 12).

Once ready for the power morcellation, under vision using the telescopic systems and monitors as per routine practice of the surgery, through the inflated abdominal cavity/or through the in-bag morcellation device ie; the "Safety Isolation Bag" contain the specimen, introduce the morcellator hand piece with the blunt tip obturator. Once the hand piece unit with blunt tip obturator entered into the abdominal cavity or into the "Safety Isolation Bag" withdraw the blunt tip obturator and then introduce the cutter blade with double decker washers placed on its head. Now place the "morcellator handle head cap" and introduce the tenaculam or hand instrument to hold the tissue through the opening of the "morcellator handle head cap" (123) and then pass it through the double decker washer and also through the cutter blade tube. These procedures are performed under full vision and keeping the abdominal cavity or the safety Isolation bag in inflated stage for proper vision throughout the procedure. Hold the tissues to be morcellated with tenaculam/grasper and perform the morcellation procedure as per the normal practices and medical protocol.

Once the morcellator motor drive unit (MDU) is switched ON and the rotor cable is connected to the motor drive unit, and the foot pedal switch is activated, it rotates the rotor cable which in turn rotates the "adapter lock mechanism" of the cylindrical head of the cable which is inserted and connected to the "rotor locking knob" of the morcellator handle and thereby it rotates the cutter blade of the morcellator and enable cutting of the tissues. And the core guard position can be adjusted by turning the trocar sheath over the threaded portion as it is connected on the threaded ring on the handle as shown (122a) so that the coring of the tissues can be prevented and the cutter blade tip will be under vision throughout the procedure.

Once the uterus/fibroids are morcellated, the tenaculam/grasper is withdrawn and use suction and irrigation system to wash and clean the abdominal cavity. Then remove the Morcellator hand piece assembly from the abdominal cavity and or remove the "Safety Isolation Bag" incase if the morcellation was done as an in-bag procedure. Once the morcellator hand piece assembly is withdrawn from the patient's body, each part of the hand piece system is dismantled and cleaned well and re-sterilized for future usage.

We have brought out the novel features of the invention by explaining some of the preferred embodiments under the invention, enabling those skilled in the art to understand and visualize our invention. It is also to be understood that the invention is not limited in its application to the details set forth in the above description. Although the invention has been described in considerable detail with reference to certain preferred embodiments thereof, various modifications can be made without departing from the spirit and scope of the invention as described herein above and as defined in the following claims.

I claim:

1. A reusable universal tissue morcellator system comprising a hollow tubed morcellator hand piece locked with a flexible rotor cable connected to a motor drive unit (MDU) on one side and the morcellator hand piece comprising a morcellator trocar sheath having a trocar head and a trocar cannula tube on another side, wherein an obturator is inserted into the morcellator hand piece to push the morcellator hand piece to insert the morcellator hand piece into an abdominal cavity, and wherein upon insertion of the morcellator hand piece into the abdominal cavity, the obturator is withdrawn from the morcellator hand piece and a cutter blade is inserted in the morcellator hand piece connected to the motor drive unit using the rotor cable, characterized in that:
   a) the morcellator hand piece comprises a fixed size morcellator handle with the morcellator trocar sheath having the trocar head and the trocar cannula tube assembled with the trocar head, wherein the trocar head is provided with an internal threading for assembling to the morcellator handle, wherein the trocar cannula tube is selected from a plurality of cannula tubes with different diameters and different lengths;
   b) the cutter blade comprises a cutter blade head with two sets of pin-holes comprising a first set of holes and a second set of holes, with the first set of holes to enable the cutter blade to keep in a deactivated position while not in use during morcellation and the second set of holes to keep the cutter blade locked to the morcellator handle so that a cutting edge of the cutter blade is exposed for the morcellation, and wherein the cutter blade includes double step projections with grooves to place a double decker washer having double locking projections; and
   c) the obturator comprises i) a head end on one end with one set of locking pin-holes so that the obturator gets locked to the morcellator handle once inserted properly, ii) a conical blunt tip with a reverse tapering on another end and a rod connected in between the two ends;
   d) the double decker washer is provided therein for positioning to a back end of the cutter blade which gets tightly fixed on the cutter blade head and functions as pneumoseal, and as well as enables the passage of tentaculum/hand instruments while blocking leakage of gas, once the instrument is withdrawn through the double decker washer;
   e) the motor drive unit comprises a control panel with a touch screen operating system as well as a manual operating system having 4 to 10 inch wide touch screen with inbuilt installation tutorial videos and procedure videos having audio alerts, wherein the motor drive unit comprises a provision to set up speed of the cutter blade between 50 RPM to 3000 RPM manually and/or remotely, wherein the motor drive unit further comprises an USB port for editing or updating programs of an interface of the touch screen, wherein the provision exists to control the speed of the motor drive unit includes: b) speed control buttons on the morcellator handle; or c) a speed control mechanism provided on a foot pedal; or d) a remote control arrangement.

2. The reusable universal tissue morcellator system as claimed in claim 1, wherein one end of the flexible rotor cable is connected to the control panel of the motor drive unit and another end of the rotor cable is provided with a cylindrical head provided with an adaptor lock mechanism, wherein the cylindrical head is inserted and locked into a tubular hollow area of the morcellator handle and connected to a rotor locking knob provided inside a hollow tube of the morcellator handle, enabling the handle to lock with the rotor cable's cylindrical head, once inserted inside the morcellator handle followed by locking by a handle locking ring.

3. The reusable universal tissue morcellator system as claimed in claim 2, wherein the cylindrical head of the rotor cable is connected to the flexible rotor cable, and wherein vertical projections are provided on the cylindrical head of the rotor cable, and wherein the vertical projections are fitted into the grooves provided inside the hollow tube of the morcellator handle so as to stabilize and immobilize it, once the body of the cylindrical head of the rotor cable is inserted inside the hollow tube of the morcellator handle.

4. The reusable universal tissue morcellator system as claimed in claim 2, wherein the cylindrical head of the rotor cable is made by welding the adaptor lock mechanism comprising of a metallic tube of 4-8 mm diameter and 2 to 5 cm length having cross cut groove to a depth of about 1 cm at one end and another end is welded to a metallic portion of the inner flexible rotor cable and assembled inside an acrylic tube within a ball-bearing assembly and covered and packed tightly within a cylindrical body so that the cylindrical head gets closely placed into the hollow tube of the morcellator handle and the adaptor lock mechanism gets locked to the rotor locking knob inside the morcellator handle.

5. The reusable universal tissue morcellator system as claimed in claim 1, wherein a front end of the morcellator handle is provided with an externally threaded portion and is connected to the morcellator trocar sheath to form the morcellator hand piece through which the cutter blade/the obturator is insertable via a cutter blade/an obturator insertion area provided with a locking pin and an unlocking button mechanism, and wherein a rear end of the morcellator handle comprises provision to assemble a morcellator handle head cap.

6. The reusable universal tissue morcellator system as claimed in claim 1, wherein the motor drive unit comprises the touch screen operating system, with RPM indicators, an audio alarm on cutting speed, warning indicators/alarm, and manual operating buttons, and wherein said motor drive unit is designed in such a way that it is usable in urological surgeries (TURP), in addition to gynaecological surgeries and general surgeries, by altering the programs on the control panel.

7. The reusable universal tissue morcellator system as claimed in claim 1, wherein the provision to control the speed of the motor drive unit comprises the speed control mechanism provided on the foot pedal, wherein the foot pedal is provided with an activation button to activate said system during the surgical procedures.

8. The reusable universal tissue morcellator system as claimed in claim 1, wherein a number of pin-holes in the one set of locking pin-holes is ranging from 6 to 10.

9. The reusable universal tissue morcellator system as claimed in claim 8, wherein the obturator is inserted through an obturator/a cutter blade insertion area of the morcellator hand piece and gets locked on to the locking pinholes of the obturator by a pin locking mechanism.

10. The reusable universal tissue morcellator system as claimed in claim 1, wherein the plurality of cannula tubes are associated with different diameters and lengths, wherein the diameter of each of the plurality of cannula tubes is selected from 4 mm, 6 mm, 10 mm, 15 mm, 18 mm and 22 mm and the length of each of the plurality of cannula tubes is ranging from 4 to 18 cm.

11. The reusable universal tissue morcellator system as claimed in claim 10, wherein the distal end of the cannula tube is obliquely cut, and wherein the trocar head is connectable to an externally threaded portion of a front end of the morcellator handle which works as the outer sheath for the cutter blade and also as a core guard to prevent coring of tissues and enabling pealing of tissues during morcellation.

12. The reusable universal tissue morcellator system as claimed in claim 10, wherein a core-guard position is changed by rotating the morcellator trocar sheath over an externally threaded portion to anterior/posterior/right side/left side of a fibroid to facilitate proper morcellation without coring the tissues and for proper vision of tip of the cutter blade throughout the surgery.

13. The reusable universal tissue morcellator system as claimed in claim 1, wherein the cutter blade comprises the cutter blade head with an opening and a cutter tube, wherein a distal end of cutter tube either has circular sharp edge or circular sharp serrated edge for effective cutting, wherein the cutter blade includes one or two stopper rings provided at a distance ranging from 4 to 8 cm from the nearest set of the pin: holes of the two sets of pin-holes of the cutter blade head.

14. The reusable universal tissue morcellator system as claimed in claim 13, wherein the cutter blade head is provided with specially matching of the double step projections with the grooves to enable double locking of the double decker washer for enhanced fitting as well as to prevent gas leaking so that the double decker washer does not come out easily during extraction of tissues.

15. The reusable universal tissue morcellator system as claimed in claim 13, wherein an inner hole entry of the cutter blade head comprises chamfering to enable the free opening and closing of inner valve diaphragms of the double decker washer, once positioned on to the cutter blade head having the double step projections with the grooves while inserting and withdrawing the hand instrument during morcellation.

16. The reusable universal tissue morcellator system as claimed in claim 1, wherein the double decker washer placed on a cutter blade head end comprises two separate diaphragms and the upper diaphragm comprises 4 mm to 20 mm diameter, chosen based on the hand instruments used, with single straight cut opening in the center within a circular projection and the bottom diaphragm which is one to two cm below the upper diaphragm with a cross cut multi flap opening at the middle with 4 mm to 20 mm diameters to enable the passage of the tentaculum/hand-instruments and also to block gas leakage, once the instrument is withdrawn through the double decker washer.

17. The reusable universal tissue morcellator system as claimed in claim 16, wherein the inner multi flap diaphragm of the double decker washer is made with 4 flaps and the external opening is made with single cut and not in line with the inside cutting, enabling more effective pneumoseal effect.

18. The reusable universal tissue morcellator system as claimed in claim 16, wherein the instruments are inserted through the outer opening of the double decker washer and the inner multi flap opening of the double decker washer acts as an additional pneumoseal when the instruments are withdrawn and the bottom portion of the double decker washer is with double locking projections which gets tightly fixed on the cutter tubes' double step projections with grooves on its head.

19. The reusable universal tissue morcellator system as claimed in claim 1, wherein a length adjusting ring of the morcellator hand piece is capable of tightening and adjusting as per the length needed inside the abdominal cavity during the morcellation procedure for the surgeon and said length adjusting ring is made of fiber, Teflon or stainless steel with a threaded screw.

20. The reusable universal tissue morcellator system as claimed in claim 1, wherein an exposed portion of the head end of the cutter blade is covered once the cutter blade is inserted and locked with a morcellator handle head cap provided with a 25 mm diameter opening at the head-end for inserting hand instruments to extract tissues while morcellation and a threaded mouth to fix it to the morcellator handle.

\* \* \* \* \*